(12) United States Patent
Zhou et al.

(10) Patent No.: US 7,015,155 B2
(45) Date of Patent: Mar. 21, 2006

(54) ELASTOMERIC ADHESIVE

(75) Inventors: Peiguang Zhou, Appleton, WI (US); Cristian M. Neculescu, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 287 days.

(21) Appl. No.: 10/187,681

(22) Filed: Jul. 2, 2002

(65) Prior Publication Data

US 2004/0005834 A1 Jan. 8, 2004

(51) Int. Cl.
  *B32B 27/04* (2006.01)
  *B32B 27/12* (2006.01)

(52) U.S. Cl. .............. 442/149; 442/104; 442/328; 442/329; 442/382; 442/394; 442/400; 442/401; 428/343; 428/355 R; 156/60; 156/196; 156/229

(58) Field of Classification Search ........... 442/149, 442/104, 328, 329, 382, 394, 400, 401; 428/343, 428/355 R; 156/60, 196, 229
  See application file for complete search history.

(56) References Cited

U.S. PATENT DOCUMENTS

| | | |
|---|---|---|
| 2,206,761 A | 7/1940 | Bergstein |
| 2,266,761 A | 12/1941 | Jackson, Jr. et al. |
| 2,357,392 A | 9/1944 | Francis, Jr. |
| 2,464,301 A | 3/1949 | Francis, Jr. |
| 2,483,405 A | 10/1949 | Francis, Jr. |
| 2,957,512 A | 10/1960 | Wade et al. |
| 2,957,852 A | 10/1960 | Frankenburg et al. |
| 3,186,893 A | 6/1965 | Mercer |
| 3,338,992 A | 8/1967 | Kinney |

(Continued)

FOREIGN PATENT DOCUMENTS

| | | |
|---|---|---|
| CA | 2165486 | 6/1996 |
| DE | 34 23 644 | 1/1986 |
| DE | 37 34 963 | 4/1988 |
| EP | 0 155 636 | 9/1985 |
| EP | 0 172 037 | 2/1986 |
| EP | 0 217 032 | 4/1987 |
| EP | 0 239 080 | 9/1987 |
| EP | 0 330 716 A2 | 9/1989 |
| EP | 0 380 781 | 8/1990 |
| EP | 0 396 800 | 11/1990 |
| EP | 0 456 885 | 11/1991 |
| EP | 0 547 497 | 6/1993 |
| EP | 0 582 569 | 2/1994 |
| EP | 0 604 731 | 7/1994 |
| EP | 0 617 939 | 10/1994 |
| EP | 0 688 550 | 12/1995 |
| EP | 0 689 815 | 1/1996 |
| EP | 0 713 546 | 5/1996 |
| EP | 0 743 052 | 11/1996 |
| EP | 0 753 292 | 1/1997 |
| EP | 0 761 193 | 3/1997 |
| EP | 0 761 194 | 3/1997 |
| EP | 0 763 353 | 3/1997 |
| EP | 0 787 474 | 8/1997 |
| EP | 0 802 251 A | 10/1997 |

(Continued)

*Primary Examiner*—Terrel Morris
*Assistant Examiner*—Andrew T Piziali
(74) *Attorney, Agent, or Firm*—Pauley Petersen & Erickson

(57) ABSTRACT

Elastomeric adhesive compositions including a high softening point tackifier resin in combination with a base polymer can be used to create laminates having effective adhesion and elastic properties. The compositions may also include a low softening point additive, and/or an antioxidant. Facing layers, such as nonwoven webs and/or films, can be laminated to both surfaces of the elastomeric compositions to form laminates. A method of making such compositions and laminates involves forming the compositions into elastomeric adhesive films.

55 Claims, 5 Drawing Sheets

U.S. PATENT DOCUMENTS

| | | |
|---|---|---|
| 3,341,394 A | 9/1967 | Kinney |
| 3,371,668 A | 3/1968 | Johnson |
| 3,391,048 A | 7/1968 | Dyer et al. |
| 3,439,085 A | 4/1969 | Hartmann |
| 3,449,187 A | 6/1969 | Bobkowicz |
| 3,468,748 A | 9/1969 | Bassett |
| 3,489,148 A | 1/1970 | Duncan et al. |
| 3,502,538 A | 3/1970 | Petersen |
| 3,502,763 A | 3/1970 | Hartmann |
| 3,542,615 A | 11/1970 | Dobo et al. |
| 3,575,782 A | 4/1971 | Hansen |
| 3,616,129 A | 10/1971 | Sager |
| 3,629,047 A | 12/1971 | Davison |
| 3,669,823 A | 6/1972 | Wood |
| 3,673,026 A | 6/1972 | Brown |
| 3,676,242 A | 7/1972 | Prentice |
| 3,689,342 A | 9/1972 | Vogt et al. |
| 3,692,618 A | 9/1972 | Dorschner et al. |
| 3,752,613 A | 8/1973 | Vogt et al. |
| 3,773,590 A | 11/1973 | Morgan |
| 3,802,817 A | 4/1974 | Matsuki et al. |
| 3,806,289 A | 4/1974 | Schwarz |
| 3,836,416 A | 9/1974 | Ropiequet |
| 3,838,692 A | 10/1974 | Levesque |
| 3,849,241 A | 11/1974 | Butin et al. |
| 3,857,144 A | 12/1974 | Bustin |
| 3,860,003 A | 1/1975 | Buell |
| 3,890,184 A | 6/1975 | Morgan |
| 3,904,465 A | 9/1975 | Haase et al. |
| 3,912,567 A | 10/1975 | Schwartz |
| 3,917,448 A | 11/1975 | Wood |
| 3,932,328 A | 1/1976 | Korpman |
| 3,949,128 A | 4/1976 | Ostermeier |
| 3,949,130 A | 4/1976 | Sabee et al. |
| 3,973,063 A | 8/1976 | Clayton |
| 3,978,185 A | 8/1976 | Buntin et al. |
| 3,979,050 A | 9/1976 | Cilia |
| 4,013,816 A | 3/1977 | Sabee et al. |
| 4,028,292 A | 6/1977 | Korpman |
| 4,038,346 A | 7/1977 | Feeney |
| 4,080,348 A | 3/1978 | Korpman |
| 4,090,385 A | 5/1978 | Packard |
| 4,107,364 A | 8/1978 | Sisson |
| 4,135,037 A | 1/1979 | Udipi et al. |
| 4,148,676 A | 4/1979 | Paquette et al. |
| 4,209,563 A | 6/1980 | Sisson |
| 4,211,807 A | 7/1980 | Yazawa et al. |
| 4,239,578 A | 12/1980 | Gore |
| 4,241,123 A | 12/1980 | Shih |
| 4,248,652 A | 2/1981 | Civardi et al. |
| 4,259,220 A | 3/1981 | Bunnelle et al. |
| 4,285,998 A | 8/1981 | Thibodeau |
| 4,300,562 A | 11/1981 | Pieniak |
| 4,302,495 A | 11/1981 | Marra |
| 4,303,571 A | 12/1981 | Jansen et al. |
| 4,304,234 A | 12/1981 | Hartmann |
| 4,310,594 A | 1/1982 | Yamazaki et al. |
| 4,319,572 A | 3/1982 | Widlund et al. |
| 4,323,534 A | 4/1982 | DesMarais |
| 4,333,782 A | 6/1982 | Pieniak |
| 4,340,558 A | 7/1982 | Hendrickson |
| 4,340,563 A | 7/1982 | Appel et al. |
| 4,375,446 A | 3/1983 | Fujii et al. |
| 4,402,688 A | 9/1983 | Julemont |
| 4,405,397 A | 9/1983 | Teed |
| 4,413,623 A | 11/1983 | Pieniak |
| 4,417,935 A | 11/1983 | Spencer |
| 4,418,123 A | 11/1983 | Bunnelle et al. |
| 4,438,167 A | 3/1984 | Schwarz |
| 4,440,819 A | 4/1984 | Rosser et al. |
| 4,490,427 A | 12/1984 | Grant et al. |
| 4,496,417 A | 1/1985 | Haake et al. |
| 4,500,316 A | 2/1985 | Damico |
| 4,507,163 A | 3/1985 | Menard |
| 4,522,863 A | 6/1985 | Keck et al. |
| 4,525,407 A | 6/1985 | Ness |
| 4,543,099 A * | 9/1985 | Bunnelle et al. ........ 604/385.24 |
| 4,548,859 A | 10/1985 | Kline et al. |
| 4,552,795 A | 11/1985 | Hansen et al. |
| 4,555,811 A | 12/1985 | Shimalla |
| 4,572,752 A | 2/1986 | Jensen et al. |
| 4,586,199 A | 5/1986 | Birring |
| D284,036 S | 6/1986 | Birring |
| 4,606,964 A | 8/1986 | Wideman |
| 4,618,384 A | 10/1986 | Sabee |
| 4,626,305 A | 12/1986 | Suzuki et al. |
| 4,636,419 A | 1/1987 | Madsen et al. |
| 4,640,859 A | 2/1987 | Hansen et al. |
| 4,644,045 A | 2/1987 | Fowells |
| 4,652,487 A | 3/1987 | Morman |
| 4,656,081 A | 4/1987 | Ando et al. |
| 4,657,793 A | 4/1987 | Fisher |
| 4,657,802 A | 4/1987 | Morman |
| 4,661,389 A | 4/1987 | Mudge et al. |
| 4,663,220 A | 5/1987 | Wisneski et al. |
| 4,666,542 A | 5/1987 | De Jonckheere |
| 4,675,068 A | 6/1987 | Lundmark |
| 4,683,877 A | 8/1987 | Ersfeld et al. |
| 4,687,477 A | 8/1987 | Suzuki et al. |
| 4,692,368 A | 9/1987 | Taylor et al. |
| 4,692,371 A | 9/1987 | Morman et al. |
| 4,698,242 A | 10/1987 | Salerno |
| 4,704,116 A | 11/1987 | Enloe |
| 4,718,901 A | 1/1988 | Singheimer |
| 4,719,261 A | 1/1988 | Bunnelle et al. |
| 4,720,415 A | 1/1988 | Vander Wielen et al. |
| 4,725,468 A | 2/1988 | McIntyre |
| 4,726,874 A | 2/1988 | VanVliet |
| 4,734,311 A | 3/1988 | Sokolowski |
| 4,734,320 A | 3/1988 | Ohira et al. |
| 4,734,447 A | 3/1988 | Hattori et al. |
| 4,735,673 A | 4/1988 | Piron |
| 4,756,942 A | 7/1988 | Aichele |
| 4,761,198 A | 8/1988 | Salerno |
| 4,762,582 A | 8/1988 | de Jonckheere |
| 4,775,579 A | 10/1988 | Hagy et al. |
| 4,777,080 A | 10/1988 | Harris, Jr. et al. |
| 4,789,699 A * | 12/1988 | Kieffer et al. .............. 524/271 |
| 4,798,603 A | 1/1989 | Meyer et al. |
| 4,801,345 A | 1/1989 | Dussaud et al. |
| 4,801,482 A | 1/1989 | Goggans et al. |
| 4,803,117 A | 2/1989 | Daponte |
| 4,804,577 A | 2/1989 | Hazelton et al. |
| 4,818,597 A | 4/1989 | DaPonte et al. |
| 4,826,415 A | 5/1989 | Mende |
| 4,837,715 A | 6/1989 | Ungpiyakul et al. |
| 4,842,666 A | 6/1989 | Werenicz |
| 4,854,985 A | 8/1989 | Soderlund et al. |
| 4,854,989 A | 8/1989 | Singheimer |
| 4,863,779 A | 9/1989 | Daponte |
| 4,867,735 A | 9/1989 | Wogelius |
| 4,874,447 A | 10/1989 | Hazelton et al. |
| 4,879,170 A | 11/1989 | Radwanski et al. |
| 4,883,482 A | 11/1989 | Gandrez et al. |
| 4,883,549 A | 11/1989 | Frost et al. |
| 4,891,258 A | 1/1990 | Fahrenkrug |
| 4,892,536 A | 1/1990 | DesMarais et al. |
| 4,892,903 A | 1/1990 | Himes |
| 4,900,619 A | 2/1990 | Ostrowski et al. |
| 4,906,507 A | 3/1990 | Grynaeus et al. |
| 4,908,247 A | 3/1990 | Baird et al. |

| Patent No. | Date | Inventor |
|---|---|---|
| 4,908,253 A | 3/1990 | Rasmussen |
| 4,910,064 A | 3/1990 | Sabee |
| 4,917,696 A | 4/1990 | De Jonckheere |
| 4,917,746 A | 4/1990 | Kons et al. |
| 4,929,492 A | 5/1990 | Carey, Jr. et al. |
| 4,935,021 A | 6/1990 | Huffman et al. |
| 4,938,757 A | 7/1990 | Van Gompel et al. |
| 4,938,821 A | 7/1990 | Soderlund et al. |
| 4,939,016 A | 7/1990 | Radwanski et al. |
| 4,940,464 A | 7/1990 | Van Gompel et al. |
| 4,965,122 A | 10/1990 | Morman |
| 4,968,313 A | 11/1990 | Sabee |
| 4,970,259 A | 11/1990 | Mitchell et al. |
| 4,977,011 A | 12/1990 | Smith |
| 4,984,584 A | 1/1991 | Hansen et al. |
| 4,994,508 A | 2/1991 | Shiraki et al. |
| 4,995,928 A | 2/1991 | Sabee |
| 4,998,929 A | 3/1991 | Bjorksund et al. |
| 5,000,806 A | 3/1991 | Merkatoris et al. |
| 5,002,815 A | 3/1991 | Yamanaka et al. |
| 5,005,215 A | 4/1991 | McIlquham |
| 5,013,785 A | 5/1991 | Mizui |
| 5,028,646 A | 7/1991 | Miller et al. |
| 5,032,120 A | 7/1991 | Freeland et al. |
| 5,034,008 A | 7/1991 | Breitkopf |
| 5,045,133 A | 9/1991 | DaPonte et al. |
| 5,046,272 A | 9/1991 | Vogt et al. |
| 5,060,349 A | 10/1991 | Walton et al. |
| 5,073,436 A | 12/1991 | Antonacci et al. |
| 5,093,422 A | 3/1992 | Himes |
| 5,100,435 A | 3/1992 | Onwumere |
| 5,104,116 A | 4/1992 | Pohjola |
| 5,108,820 A | 4/1992 | Kaneko et al. |
| 5,112,889 A | 5/1992 | Miller et al. |
| 5,114,087 A | 5/1992 | Fisher et al. |
| 5,116,662 A | 5/1992 | Morman |
| 5,147,487 A | 9/1992 | Nomura et al. |
| 5,149,741 A * | 9/1992 | Alper et al. ............... 525/95 |
| 5,163,932 A | 11/1992 | Nomura et al. |
| D331,627 S | 12/1992 | Igaue et al. |
| 5,169,706 A | 12/1992 | Collier, IV et al. |
| 5,169,712 A | 12/1992 | Tapp |
| 5,176,668 A | 1/1993 | Bernardin |
| 5,176,672 A | 1/1993 | Bruemmer et al. |
| 5,186,779 A | 2/1993 | Tubbs |
| 5,192,606 A | 3/1993 | Proxmire et al. |
| 5,198,281 A | 3/1993 | Muzzy et al. |
| 5,200,246 A | 4/1993 | Sabee |
| 5,204,429 A | 4/1993 | Kaminsky et al. |
| D335,707 S | 5/1993 | Igaue et al. |
| 5,209,801 A | 5/1993 | Smith |
| 5,219,633 A | 6/1993 | Sabee |
| 5,224,405 A | 7/1993 | Pohjola |
| 5,226,992 A | 7/1993 | Morman |
| 5,229,191 A | 7/1993 | Austin |
| 5,232,777 A | 8/1993 | Sipinen et al. |
| 5,236,430 A | 8/1993 | Bridges |
| 5,236,770 A | 8/1993 | Assent et al. |
| 5,238,733 A | 8/1993 | Joseph et al. |
| 5,246,433 A | 9/1993 | Hasse et al. |
| D340,283 S | 10/1993 | Igaue et al. |
| 5,252,170 A | 10/1993 | Schaupp |
| 5,259,902 A | 11/1993 | Muckenfuhs |
| 5,260,126 A | 11/1993 | Collier, IV et al. |
| 5,272,236 A | 12/1993 | Lai et al. |
| 5,278,272 A | 1/1994 | Lai et al. |
| 5,288,791 A | 2/1994 | Collier, IV et al. |
| 5,290,842 A | 3/1994 | Sasaki et al. |
| 5,296,080 A | 3/1994 | Merkatoris et al. |
| 5,304,599 A | 4/1994 | Himes |
| 5,308,345 A | 5/1994 | Herrin |
| 5,312,500 A | 5/1994 | Kurihara et al. |
| 5,324,580 A | 6/1994 | Allan et al. |
| 5,332,613 A | 7/1994 | Taylor et al. |
| 5,334,437 A | 8/1994 | Zafiroglu |
| 5,334,446 A | 8/1994 | Quantrille et al. |
| 5,336,545 A | 8/1994 | Morman |
| 5,336,552 A | 8/1994 | Strack et al. |
| 5,342,341 A | 8/1994 | Igaue et al. |
| 5,342,469 A | 8/1994 | Bodford et al. |
| 5,360,854 A | 11/1994 | Bozich, Jr. |
| 5,364,382 A | 11/1994 | Latimer et al. |
| 5,366,793 A | 11/1994 | Fitts, Jr. et al. |
| 5,376,198 A | 12/1994 | Fahrenkrug et al. |
| 5,376,430 A | 12/1994 | Swenson et al. |
| 5,382,400 A | 1/1995 | Pike et al. |
| 5,385,775 A | 1/1995 | Wright |
| 5,389,173 A | 2/1995 | Merkatoris et al. |
| 5,389,438 A * | 2/1995 | Miller et al. .......... 428/355 RA |
| 5,393,599 A | 2/1995 | Quantrille et al. |
| 5,399,219 A | 3/1995 | Roessler et al. |
| 5,405,682 A | 4/1995 | Shawyer et al. |
| 5,407,507 A | 4/1995 | Ball |
| 5,411,618 A | 5/1995 | Jocewicz, Jr. |
| 5,413,654 A | 5/1995 | Igaue et al. |
| 5,413,849 A | 5/1995 | Austin et al. |
| 5,415,644 A | 5/1995 | Enloe |
| 5,415,649 A | 5/1995 | Watanabe et al. |
| 5,415,925 A | 5/1995 | Austin et al. |
| 5,422,172 A | 6/1995 | Wu |
| 5,425,987 A | 6/1995 | Shawver et al. |
| 5,429,629 A | 7/1995 | Latimer et al. |
| 5,429,694 A | 7/1995 | Herrmann |
| 5,429,856 A | 7/1995 | Krueger et al. |
| 5,431,644 A | 7/1995 | Sipinen et al. |
| 5,431,991 A | 7/1995 | Quantrille et al. |
| 5,447,462 A | 9/1995 | Smith et al. |
| 5,447,508 A | 9/1995 | Numano et al. |
| 5,449,353 A | 9/1995 | Watanabe et al. |
| 5,464,401 A | 11/1995 | Hasse et al. |
| 5,472,775 A | 12/1995 | Obijeski et al. |
| 5,476,458 A | 12/1995 | Glaug et al. |
| 5,476,563 A | 12/1995 | Nakata |
| 5,484,645 A | 1/1996 | Lickfield et al. |
| 5,486,166 A | 1/1996 | Bishop et al. |
| 5,490,846 A | 2/1996 | Ellis et al. |
| 5,496,298 A | 3/1996 | Kuepper et al. |
| 5,498,468 A | 3/1996 | Blaney |
| 5,500,075 A | 3/1996 | Herrmann |
| 5,501,679 A | 3/1996 | Krueger et al. |
| 5,509,915 A | 4/1996 | Hanson et al. |
| 5,514,470 A | 5/1996 | Haffner et al. |
| 5,516,476 A | 5/1996 | Haggard et al. |
| 5,523,146 A | 6/1996 | Bodford et al. |
| 5,527,300 A | 6/1996 | Sauer |
| 5,531,850 A | 7/1996 | Herrmann |
| 5,534,330 A | 7/1996 | Groshens |
| 5,536,563 A | 7/1996 | Shah et al. |
| 5,540,796 A | 7/1996 | Fries |
| 5,540,976 A | 7/1996 | Shawver et al. |
| 5,543,206 A | 8/1996 | Austin et al. |
| 5,545,158 A | 8/1996 | Jessup |
| 5,545,285 A | 8/1996 | Johnson |
| 5,549,964 A | 8/1996 | Shohji et al. |
| 5,569,232 A | 10/1996 | Roe et al. |
| 5,575,783 A | 11/1996 | Clear et al. |
| 5,576,090 A | 11/1996 | Suzuki |
| 5,582,668 A | 12/1996 | Kling |
| 5,591,152 A | 1/1997 | Buell et al. |
| 5,591,792 A | 1/1997 | Hattori et al. |
| 5,595,618 A | 1/1997 | Fries et al. |
| 5,597,430 A | 1/1997 | Rasche |

| Patent Number | Date | Inventor(s) |
|---|---|---|
| 5,612,118 A | 3/1997 | Schleinz et al. |
| 5,614,276 A | 3/1997 | Petsetakis |
| 5,620,780 A | 4/1997 | Krueger et al. |
| 5,624,740 A | 4/1997 | Nakata |
| 5,626,573 A | 5/1997 | Igaue et al. |
| 5,628,856 A | 5/1997 | Dobrin et al. |
| 5,645,672 A | 7/1997 | Dobrin |
| 5,652,041 A | 7/1997 | Buerger et al. |
| 5,660,664 A | 8/1997 | Herrmann |
| 5,663,228 A | 9/1997 | Sasaki et al. |
| 5,669,897 A | 9/1997 | Lavon et al. |
| 5,674,216 A | 10/1997 | Buell et al. |
| 5,680,653 A | 10/1997 | Mathis et al. |
| 5,681,302 A | 10/1997 | Melbye et al. |
| 5,683,787 A | 11/1997 | Boich et al. |
| 5,690,626 A | 11/1997 | Suzuki et al. |
| 5,691,034 A | 11/1997 | Krueger et al. |
| 5,693,038 A | 12/1997 | Suzuki et al. |
| 5,695,849 A | 12/1997 | Shawver et al. |
| 5,702,378 A | 12/1997 | Widlund et al. |
| 5,707,709 A | 1/1998 | Blake |
| 5,709,921 A | 1/1998 | Shawver |
| 5,720,838 A | 2/1998 | Nakata |
| 5,733,635 A | 3/1998 | Terakawa et al. |
| 5,733,822 A | 3/1998 | Gessner et al. |
| 5,735,839 A | 4/1998 | Kawaguchi et al. |
| 5,736,219 A | 4/1998 | Suehr et al. |
| 5,746,731 A | 5/1998 | Hisada |
| 5,749,865 A | 5/1998 | Yamamoto et al. |
| 5,749,866 A | 5/1998 | Roe et al. |
| 5,766,389 A | 6/1998 | Brandon et al. |
| 5,766,737 A | 6/1998 | Willey et al. |
| 5,769,838 A | 6/1998 | Buell et al. |
| 5,769,993 A | 6/1998 | Baldauf |
| 5,772,649 A | 6/1998 | Siudzinski |
| 5,773,373 A | 6/1998 | Wynne et al. |
| 5,773,374 A | 6/1998 | Wood et al. |
| 5,788,804 A | 8/1998 | Horsting |
| 5,789,065 A | 8/1998 | Haffner et al. |
| 5,789,328 A | 8/1998 | Kurihara et al. |
| 5,789,474 A | 8/1998 | Lu et al. |
| 5,790,983 A | 8/1998 | Rosch et al. |
| 5,800,903 A | 9/1998 | Wood et al. |
| 5,804,021 A | 9/1998 | Abuto et al. |
| 5,804,286 A | 9/1998 | Quantrille et al. |
| 5,814,176 A | 9/1998 | Proulx |
| 5,817,087 A | 10/1998 | Takabayashi et al. |
| 5,818,719 A | 10/1998 | Brandon et al. |
| 5,830,203 A | 11/1998 | Suzuki et al. |
| 5,834,089 A | 11/1998 | Jones et al. |
| 5,836,931 A | 11/1998 | Toyoda et al. |
| 5,836,932 A | 11/1998 | Buell et al. |
| 5,840,412 A | 11/1998 | Wood et al. |
| 5,840,633 A | 11/1998 | Kurihara et al. |
| 5,846,232 A | 12/1998 | Serbiak et al. |
| 5,849,001 A | 12/1998 | Torimae et al. |
| 5,856,387 A | 1/1999 | Sasaki et al. |
| 5,860,945 A | 1/1999 | Cramer et al. |
| 5,865,933 A | 2/1999 | Morin et al. |
| 5,876,392 A | 3/1999 | Hisada |
| 5,879,776 A | 3/1999 | Nakata |
| 5,882,573 A | 3/1999 | Kwok et al. |
| 5,885,656 A | 3/1999 | Goldwasser |
| 5,885,686 A | 3/1999 | Cederblad et al. |
| 5,897,546 A | 4/1999 | Kido et al. |
| 5,899,895 A | 5/1999 | Robles et al. |
| 5,902,540 A | 5/1999 | Kwok |
| 5,904,298 A | 5/1999 | Kwok et al. |
| 5,916,206 A | 6/1999 | Otsubo et al. |
| 5,921,973 A | 7/1999 | Newkirk et al. |
| 5,930,139 A | 7/1999 | Chapdelaine et al. |
| 5,931,581 A | 8/1999 | Garberg et al. |
| 5,932,039 A | 8/1999 | Popp et al. |
| 5,938,648 A | 8/1999 | LaVon et al. |
| 5,941,865 A | 8/1999 | Otsubo et al. |
| D414,262 S | 9/1999 | Ashton et al. |
| 5,952,252 A | 9/1999 | Shawver et al. |
| 5,964,970 A | 10/1999 | Woolwine et al. |
| 5,964,973 A | 10/1999 | Heath et al. |
| 5,990,377 A | 11/1999 | Chen et al. |
| 5,993,433 A | 11/1999 | St. Louis et al. |
| 5,997,521 A | 12/1999 | Robles et al. |
| 6,004,306 A | 12/1999 | Robles et al. |
| 6,009,558 A | 1/2000 | Rosch et al. |
| 6,033,502 A | 3/2000 | Coenen et al. |
| 6,045,543 A | 4/2000 | Pozniak et al. |
| 6,048,326 A | 4/2000 | Davis et al. |
| 6,057,024 A | 5/2000 | Mleziva et al. |
| 6,066,369 A | 5/2000 | Schulz et al. |
| 6,087,550 A | 7/2000 | Anderson-Fischer et al. |
| 6,090,234 A | 7/2000 | Barone et al. |
| 6,092,002 A | 7/2000 | Kastman et al. |
| 6,093,663 A | 7/2000 | Ouellette et al. |
| 6,096,668 A | 8/2000 | Abuto et al. |
| 6,123,694 A | 9/2000 | Pieniak et al. |
| 6,132,410 A | 10/2000 | Van Gompel et al. |
| 6,149,637 A | 11/2000 | Allen et al. |
| 6,152,904 A | 11/2000 | Matthews et al. |
| 6,169,848 B1 | 1/2001 | Henry |
| 6,183,587 B1 | 2/2001 | McFall et al. |
| 6,183,847 B1 | 2/2001 | Goldwasser |
| 6,197,845 B1 * | 3/2001 | Janssen et al. ............... 523/111 |
| 6,214,476 B1 | 4/2001 | Ikeda et al. |
| 6,217,690 B1 | 4/2001 | Rajala et al. |
| 6,231,557 B1 | 5/2001 | Krautkramer et al. |
| 6,238,379 B1 | 5/2001 | Keuhn, Jr. et al. |
| 6,245,050 B1 | 6/2001 | Odorzynski et al. |
| 6,245,168 B1 | 6/2001 | Coenen et al. |
| 6,260,211 B1 | 7/2001 | Rajala et al. |
| 6,279,807 B1 | 8/2001 | Crowley et al. |
| 6,290,979 B1 | 9/2001 | Roe et al. |
| 6,310,164 B1 | 10/2001 | Morizono et al. |
| 6,316,013 B1 | 11/2001 | Paul et al. |
| 6,316,687 B1 | 11/2001 | Davis et al. |
| 6,316,688 B1 | 11/2001 | Hammons et al. |
| 6,320,096 B1 | 11/2001 | Inoue et al. |
| 6,323,389 B1 | 11/2001 | Thomas et al. |
| 6,329,459 B1 | 12/2001 | Kang et al. |
| 6,364,863 B1 | 4/2002 | Yamamoto et al. |
| 6,365,659 B1 | 4/2002 | Aoyama et al. |
| 6,367,089 B1 | 4/2002 | Van Gompel et al. |
| 6,475,600 B1 | 11/2002 | Morman et al. |
| 6,537,935 B1 | 3/2003 | Seth et al. |
| 6,767,852 B1 | 7/2004 | Friderich et al. |
| 2002/0002021 A1 | 1/2002 | May et al. |
| 2002/0009940 A1 | 1/2002 | May et al. |
| 2002/0019616 A1 | 2/2002 | Thomas |
| 2002/0072561 A1 | 6/2002 | Johoji et al. |
| 2002/0081423 A1 | 6/2002 | Heffelfinger |
| 2002/0104608 A1 | 8/2002 | Welch et al. |
| 2002/0138063 A1 | 9/2002 | Kuen et al. |
| 2002/0164465 A1 | 11/2002 | Curro et al. |
| 2004/0127128 A1 | 7/2004 | Thomas |

FOREIGN PATENT DOCUMENTS

| | | |
|---|---|---|
| EP | 0 806 196 | 11/1997 |
| EP | 0 814 189 | 12/1997 |
| EP | 0 873 738 | 10/1998 |
| EP | 0 888 101 | 1/1999 |
| EP | 0 901 780 | 3/1999 |
| EP | 1 013 251 | 6/2000 |
| GB | 2 244 422 | 12/1991 |

| | | |
|---|---|---|
| GB | 2 250 921 | 6/1992 |
| GB | 2 253 131 | 9/1992 |
| GB | 2 267 024 | 11/1993 |
| GB | 2 268 389 | 1/1994 |
| IS | 92891 | 2/1992 |
| JP | 03-067646 | 3/1991 |
| WO | WO 80/00676 | 4/1980 |
| WO | WO 90/03464 | 4/1990 |
| WO | WO 91/07277 | 5/1991 |
| WO | WO 92/16371 | 10/1992 |
| WO | WO 93/15247 | 8/1993 |
| WO | WO 93/17648 | 9/1993 |
| WO | WO 94/09736 | 5/1994 |
| WO | WO 95/03443 | 2/1995 |
| WO | WO 95/04182 | 2/1995 |
| WO | WO 95/16425 | 6/1995 |
| WO | WO 95/16562 | 6/1995 |
| WO | WO 95/34264 | 12/1995 |
| WO | WO 96/13989 | 5/1996 |
| WO | WO 96/23466 | 8/1996 |
| WO | WO 96/35402 | 11/1996 |
| WO | WO 97/17046 | 5/1997 |
| WO | WO 98/14156 | 4/1998 |
| WO | WO 98/49988 | 11/1998 |
| WO | WO 98/55062 | 12/1998 |
| WO | WO 99/17926 | 4/1999 |
| WO | WO 99/24519 | 5/1999 |
| WO | WO 99/47590 | 9/1999 |
| WO | WO 99/60969 | 12/1999 |
| WO | WO 99/60970 | 12/1999 |
| WO | WO 99/60971 | 12/1999 |
| WO | WO 00/10500 | 3/2000 |
| WO | WO 00/29199 | 5/2000 |
| WO | WO 00/37003 | 6/2000 |
| WO | WO 00/37005 | 6/2000 |
| WO | WO 00/37723 | 6/2000 |
| WO | WO 00/59429 | 10/2000 |
| WO | WO 01/00053 | 1/2001 |
| WO | WO 01/32116 | 5/2001 |
| WO | WO 01/49907 | 7/2001 |
| WO | WO 01/87214 | 11/2001 |
| WO | WO 02/34184 | 5/2002 |
| WO | WO 02/053667 A2 | 7/2002 |
| WO | WO 02/053668 A2 | 7/2002 |
| WO | WO 02/060690 | 8/2002 |
| WO | WO 02/085624 A1 | 10/2002 |
| WO | WO 2004/039907 A1 | 5/2004 |

* cited by examiner

ELASTOMERIC ADHESIVE

BACKGROUND OF THE INVENTION

This invention is directed to elastomeric adhesive compositions which significantly improve decay and adhesion properties of elastomeric laminates.

Personal care garments often include elasticized portions to create a gasket-like fit around certain openings, such as waist openings and leg openings. Laminates made from conventional elastic strands and elastic attachment adhesive are often used to create such elasticized portions. However, such laminates can be rough and uncomfortable. Furthermore, such laminates may cause red-marking on a wearer's skin if the fit is too tight and may result in leakage from the garment if the fit is too loose.

Elastomeric adhesive compositions are multifunctional in the sense that they function as an elastomer in a nonwoven composite while also serving as a hot melt adhesive for bonding substrates. Elastomeric adhesive compositions in the form of elastomeric adhesive films are currently recognized as suitable for use in the manufacture of personal care articles. More particularly, elastomeric adhesive compositions can be used to bond facing materials, such as spunbond, to one another while simultaneously elasticizing the resulting laminate. The resulting laminate can be used to form an elastomeric portion of an absorbent article, such as a region surrounding a waist opening and/or a leg opening.

One drawback of current elastomeric adhesive compositions is that the compositions lose their adhesiveness when the compositions are stretched and then bonded between two nonwoven substrates. Another drawback of current elastomeric adhesive compositions is that the elasticity of the compositions (in terms of tension decay) is negatively affected when laminates including the compositions are aged at elevated temperatures, for example around 130 degrees Fahrenheit, which is commonly experienced under hot boxcar storage conditions.

It appears that the poor tension and adhesion of the current elastomeric adhesive compositions results from the chosen base polymer, tackifier, and plasticizer chemistries as well as the unbalanced ratio of polymer to low molecular weight species in the formulation.

There is a need or desire for an elastomeric adhesive composition that can be used to create elasticized portions of a personal care garment, wherein the composition does not result in high tension decay or delamination when used to produce elastic nonwoven laminates.

SUMMARY OF THE INVENTION

In response to the discussed difficulties and problems encountered in the prior art, a new elastomeric adhesive composition has been discovered.

The present invention is directed to elastomeric adhesive compositions, and laminates incorporating such elastomeric adhesive compositions, having superior elastic and adhesion properties. These compositions and laminates are particularly suitable for use in personal care product applications, medical garment applications, and industrial workwear garment applications.

The elastomeric adhesive compositions of the invention are made up of a base polymer and a high softening point tackifier resin. The compositions may also include a low softening point additive, with the low softening point additive present in an amount of between about 0% and about 20% by weight. The compositions may further include an antioxidant, with the antioxidant present in an amount of between about 0.1% and about 1.0% by weight. The tackifiers may include hydrocarbons from petroleum distillates, rosin, rosin esters, polyterpenes derived from wood, and/or polyterpenes derived from synthetic chemicals. The base polymer may include polystyrene-polyethylene-polypropylene-polystyrene (SEPS) block copolymer, styrene-isoprene-styrene (SIS), and/or styrene-butadiene-styrene (SBS) block copolymer. The base polymer is suitably present in an amount between about 30% and about 65% by weight, and the high softening point tackifier is suitably present in an amount between about 30% and about 70% by weight. The elastomeric adhesive compositions suitably have a viscosity of about 5,000 to 80,000 cps at between 350 and 400 degrees Fahrenheit. The compositions may also include elastomeric polymer strands incorporated therein to provide added reinforcement and elasticity.

Laminates can be formed using the elastomeric adhesive compositions to bond together two layers of spunbond, film, or other facing material. Laminates including the elastomeric adhesive compositions of the invention significantly improve the rate and extent of tension decay, as well as adhesion properties of the spunbond laminates compared to spunbond laminates including conventional elastomeric adhesive compositions.

The invention also includes a method of making these elastomeric adhesive compositions and laminates. These compositions can be processed by conventional hot melt equipment. The method includes the steps of forming a solid phase composition of the base polymer and the high softening point tackifier resin, then heating the solid phase composition to form a liquid phase composition. A film is then formed by extruding the liquid phase composition onto a chill roll set at a temperature of between about 10 and about 50 degrees Celsius. The film can be peeled off the chill roll while stretching the film. The film can be stretched up to about 1000%, at an output of between about 50 and about 120 grams per square meter before stretching, from a slot coat die or extrusion film die. As mentioned, elastomeric polymer strands can also be incorporated into the elastomeric adhesive compositions. A facing material, such as a nonwoven web or film, can be laminated to both surfaces of the elastomeric adhesive film, with or without the elastomeric strands incorporated into the film.

With the foregoing in mind, it is a feature and advantage of the invention to provide elastomeric adhesive compositions and laminates having improved adhesion and elastic properties. The invention also includes methods of making such elastomeric compositions and laminates.

DEFINITIONS

Figure 1:
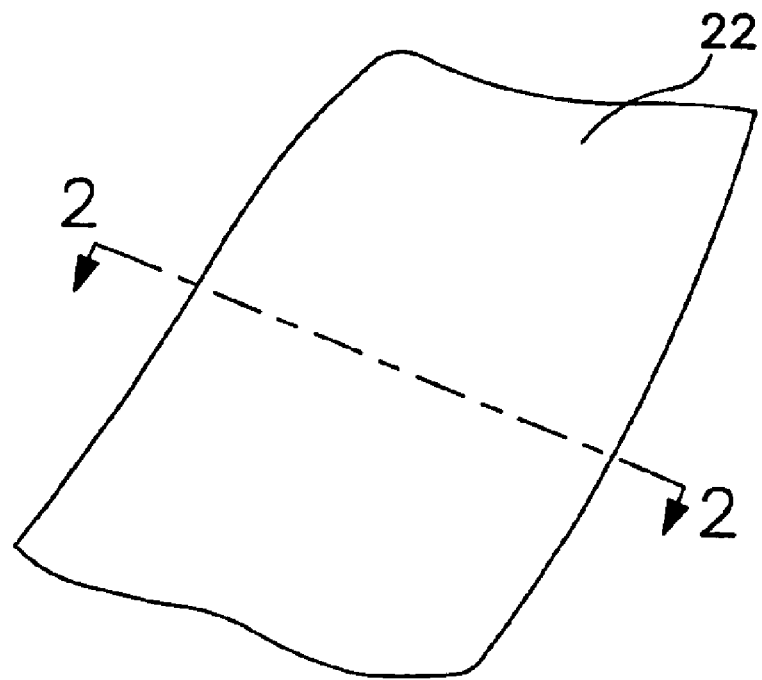
FIG. 1 is a plan view of one embodiment of an elastomeric adhesive composition of the invention.

Within the context of this specification, each term or phrase below will include the following meaning or meanings.

"Bonded" refers to the joining, adhering, connecting, attaching, or the like, of at least two elements. Two elements will be considered to be bonded together when they are bonded directly to one another or indirectly to one another, such as when each is directly bonded to intermediate elements.

"Elastic tension" refers to the amount of force per unit width required to stretch an elastic material (or a selected zone thereof) to a given percent elongation.

"Elastomeric" and "elastic" are used interchangeably to refer to a material or composite that is generally capable of recovering its shape after deformation when the deforming force is removed. Specifically, as used herein, elastic or elastomeric is meant to be that property of any material which, upon application of a biasing force, permits the material to be stretchable to a stretched biased length which is at least about 50 percent greater than its relaxed unbiased length, and that will cause the material to recover at least 40 percent of its elongation upon release of the stretching force. A hypothetical example which would satisfy this definition of an elastomeric material would be a one (1) inch sample of a material which is elongatable to at least 1.50 inches and which, upon being elongated to 1.50 inches and released, will recover to a length of less than 1.30 inches. Many elastic materials may be stretched by much more than 50 percent of their relaxed length, and many of these will recover to substantially their original relaxed length upon release of the stretching force.

"Elongation" refers to the capability of an elastic material to be stretched a certain distance, such that greater elongation refers to an elastic material capable of being stretched a greater distance than an elastic material having lower elongation.

"Film" refers to a thermoplastic film made using a film extrusion process, such as a cast film or blown film extrusion process. The term includes apertured films, slit films, and other porous films which constitute liquid transfer films, as well as films which do not transfer liquid.

"Garment" includes personal care garments, medical garments, and the like. The term "disposable garment" includes garments which are typically disposed of after 1–5 uses. The term "personal care garment" includes diapers, training pants, swim wear, absorbent underpants, adult incontinence products, feminine hygiene products, and the like. The term "medical garment" includes medical (i.e., protective and/or surgical) gowns, caps, gloves, drapes, face masks, and the like. The term "industrial workwear garment" includes laboratory coats, cover-alls, and the like.

"High softening point tackifier" refers to a tackifier having a softening point above 80 degrees Celsius, and a viscosity of at least 1500 cps at 360 degrees Fahrenheit as measured by a ring and ball method (ASTM E-28).

"Layer" when used in the singular can have the dual meaning of a single element or a plurality of elements.

"Low softening point additive" refers to a tackifier or wax or low molecular weight polymers having a softening point below 80 degrees Celsius, and a viscosity of less than 1000 cps at 360 degrees Fahrenheit as measured by a ring and ball method (ASTM E-28).

"Meltblown fiber" refers to fibers formed by extruding a molten thermoplastic material through a plurality of fine, usually circular, die capillaries as molten threads or filaments into converging high velocity gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface.

"Nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Softening point" refers to a material softening temperature, typically measured by a ring and ball type method, ASTM E-28.

"Spunbond fiber" refers to small diameter fibers which are formed by extruding molten thermoplastic material as filaments from a plurality of fine capillaries of a spinnerette having a circular or other configuration, with the diameter of the extruded filaments then being rapidly reduced as taught, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Strand" refers to an article of manufacture whose width is less than a film and is suitable for incorporating into a film, according to the present invention.

"Thermoplastic" describes a material that softens and flows when exposed to heat and which substantially returns to a nonsoftened condition when cooled to room temperature.

"Thermoset" describes a material that is capable of becoming permanently cross-linked, and the physical form of the material cannot be changed by heat without the breakdown of chemical bonds.

"Vertical filament stretch-bonded laminate" or "VF SBL" refers to a stretch-bonded laminate made using a continuous vertical filament process, as described herein.

These terms may be defined with additional language in the remaining portions of the specification.

DETAILED DESCRIPTION OF THE PRESENTLY PREFERRED EMBODIMENTS

The present invention is directed to elastomeric adhesive compositions and laminates having superior elastic and adhesion properties. The compositions and laminates can be incorporated into any suitable article, such as personal care garments, medical garments, and industrial workwear garments. More particularly, the elastomeric adhesive composites and laminates are suitable for use in diapers, training pants, swim wear, absorbent underpants, adult incontinence products, feminine hygiene products, protective medical gowns, surgical medical gowns, caps, gloves, drapes, face masks, laboratory coats, and coveralls.

A number of elastomeric components are known for use in the design and manufacture of such articles. For example, disposable absorbent articles are known to contain elasticized leg cuffs, elasticized waist portions, and elasticized fastening tabs. The elastomeric adhesive compositions and laminates of this invention may be applied to any suitable article to form such elasticized areas.

An elastomeric adhesive composition of the invention includes a base polymer and a high softening point tackifier resin. The composition may also include a low softening point additive and/or an antioxidant. The choice of polymer and tackifier is important, as is the ratio of polymer or copolymers to tackifier. Another important consideration is the ratio of low softening point additive to high softening point tackifier.

The base polymer suitably has a styrene content of between about 15% and about 45%, or between about 18% and about 30%, by weight of the base polymer. The base polymer may achieve the styrene content either by blending different polymers having different styrene co-monomer levels or by including a single base polymer that has the desired styrene co-monomer level. Generally, the higher the styrene co-monomer level is, the higher the tension is.

The base polymer may include polystyrene-polyethylene-polypropylene-polystyrene (SEPS) block copolymer, styrene-isoprene-styrene (SIS), styrene-butadiene-styrene (SBS) block copolymer, as well as combinations of any of these. One example of a suitable SEPS copolymer is available from Kraton Polymers of Belpre, Ohio, under the trade designation KRATON® G 2760. One example of a suitable SIS copolymer is available from Dexco, a division of Exxon-Mobil, under the trade designation VECTOR™. Suitably, the composition includes the base polymer in an amount between about 30% and about 65% by weight of the composition.

The base polymer suitably has a Shore A hardness of between about 20 and about 90, or between about 30 and about 80. Shore A hardness is a measure of softness, and can be measured according to ASTM D-5.

In one embodiment of the invention, the base polymer may have a melt flow rate between about 5 and about 100 grams per minute, Shore A hardness between about 20 and about 70, and may be stretched up to about 1300%.

The tackifier may include hydrocarbons from petroleum distillates, rosin, rosin esters, polyterpenes derived from wood, polyterpenes derived from synthetic chemicals, as well as combinations of any of these. A key element of the compositions of the invention is a high softening point tackifier. An example of a suitable high softening point tackifier is available from Hercules Inc. of Wilmington, Del., under the trade designation PICOLYTE™ S115. Suitably, the composition includes the high softening point tackifier in an amount between about 30% and about 70% by weight of the composition.

A low softening point additive may be included in the compositions as well. A low softening point additive typically has a softening point below 80 degrees Celsius and a viscosity of less than 1000 cps at 360 degrees Fahrenheit, while a high softening point tackifier typically has a softening point above 80 degrees Celsius and a viscosity of at least 1500 cps at 360 degrees Fahrenheit. The use of predominantly high softening point tackifiers with high viscosity is important for adhesion improvement due to enhanced cohesive strength. However, the inclusion of relatively low amounts of low softening point additives provides instantaneous surface tackiness and pressure sensitive characteristics as well as reduced melt viscosity. Suitably, the low softening point additive is present in the composition in an amount between about 0% and about 20% by weight of the composition. One example of a particularly suitable low softening point additive is paraffin wax, having a melting point of about 65 degrees Celsius.

Additionally, an antioxidant may be included in the composition of the invention, suitably in an amount between about 0.1% and about 1.0% by weight of the composition. One example of a suitable antioxidant is available from Ciba Specialty Chemicals under the trade designation IRGANOX™ 1010.

Viscosity of the formulated elastomeric adhesive composition is suitably in the range of 5,000 to 80,000 cps at 350 to 400 degrees Fahrenheit, or 10,000 to 50,000 cps at between 350 and 385 degrees Fahrenheit. The adhesive composition can be processed by conventional hot melt equipment.

The formulated elastomeric adhesive composition suitably has an elongation-to-break of between about 500% and about 1300%, or between about 600% and about 1200%. The elongation-to-break is the point of elongation at which the composition can handle no further elongation and breaks as a result.

Figure 2:
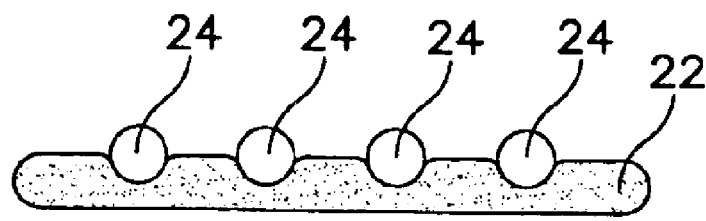
FIG. 2 is a cross-sectional view, taken along line 2—2 of FIG. 1, of another embodiment of an elastomeric adhesive composition of the invention.

One embodiment of an elastomeric adhesive composition 22 of the invention is shown in FIG. 1. In another embodiment of the invention, shown in FIG. 2 as a cross-sectional view of FIG. 1, elastomeric polymer strands 24 can be adhered to and partially embedded in the elastomeric adhesive composition 22 to further enhance laminate tension control. It will be appreciated that the strands 24 may be laid out periodically, non-periodically, and in various spacings, groupings, sizes, and compositions of elastic material according to the effect desired from the elastomeric adhesive composition 22 and the use to which it is put.

Materials suitable for use in preparing the elastic reinforcing strands 24 include diblock, triblock, tetrablock, or other multi-block elastomeric copolymers such as olefinic copolymers, including styrene-isoprene-styrene, styrene-butadiene-styrene, styrene-ethylene/butylenes-styrene, or styrene-ethylene/propylene-styrene, which may be obtained from Kraton Polymers, under the trade designation KRATON® elastomeric resin; polyurethanes, including those available from E. I. Du Pont de Nemours Co., under the trade name LYCRA® polyurethane; polyamides, including polyether block amides available from Ato Chemical Company, under the trade name PEBAX® polyether block amide; polyesters, such as those available from E. I. Du Pont de Nemours Co., under the trade name HYTREL® polyester; and single-site or metallocene-catalyzed polyolefins having density less than about 0.89 grams/cubic centimeter, available from Dow Chemical Co. under the trade name AFFINITY®.

A number of block copolymers can also be used to prepare the elastic reinforcing strands 24 used in this invention. Such block copolymers generally include an elastomeric midblock portion B and a thermoplastic endblock portion A. The block copolymers may also be thermoplastic in the sense that they can be melted, formed, and resolidified several times with little or no change in physical properties (assuming a minimum of oxidative degradation). Alternatively, the elastic strands 24 can be made of a polymer that is not thermally processable, such as LYCRA® spandex, available from E. I. Du Pont de Nemours Co., or cross-linked natural rubber in film or fiber form. Thermoset polymers and polymers such as spandex, unlike the thermoplastic polymers, once cross-linked cannot be thermally processed, but can be obtained on a spool or other form and can be stretched and applied to the strands in the same manner as thermoplastic polymers. As another alternative, the elastic strands 24 can be made of a thermoset polymer, such as AFFINITY®, available from Dow Chemical Co., that can be processed like a thermoplastic, i.e. stretched and applied, and then treated with radiation, such as electron beam radiation, gamma radiation, or UV radiation to cross-link the polymer, or use polymers that have functionality built into them such that they can be moisture-cured to cross-link the polymer, thus resulting in a polymer and the enhanced mechanical properties of a thermoset.

Endblock portion A may include a poly(vinylarene), such as polystyrene. Midblock portion B may include a substantially amorphous polyolefin such as polyisoprene, ethylene/propylene polymers, ethylene/butylenes polymers, polybutadiene, and the like, or mixtures thereof.

Suitable block copolymers useful in this invention include at least two substantially polystyrene endblock portions and at least one substantially ethylene/butylenes and isoprene or butadiene mid-block portion. A commercially available example of such a linear block copolymer is available from Kraton Polymers under the trade designation KRATON® G1657 elastomeric resin. Another suitable elastomer is KRATON® G2760.

The elastic reinforcing strands 24 may also contain blends of elastic and inelastic polymers, or of two or more elastic polymers, provided that the blend exhibits elastic properties. The strands 24 are substantially continuous in length. The strands 24 may have a circular cross-section, but may alternatively have other cross-sectional geometries such as elliptical, rectangular, triangular or multi-lobal. In one embodiment, the elastic reinforcing strands 24 may be made of the same material as the elastomeric adhesive composition 22 but in the form of elongated, rectangular strips produced from a film extrusion die having a plurality of slotted openings.

The elastomeric adhesive composition 22 is capable not only of introducing a degree of elasticity to facing materials but is also capable of providing a construction adhesive function. That is, the composition 22 adheres together the facing materials or other components with which it is in contact. It is also possible that the composition 22 does not constrict upon cooling but, instead, tends to retract to approximately its original dimension after being elongated during use in a product.

Figure 3:
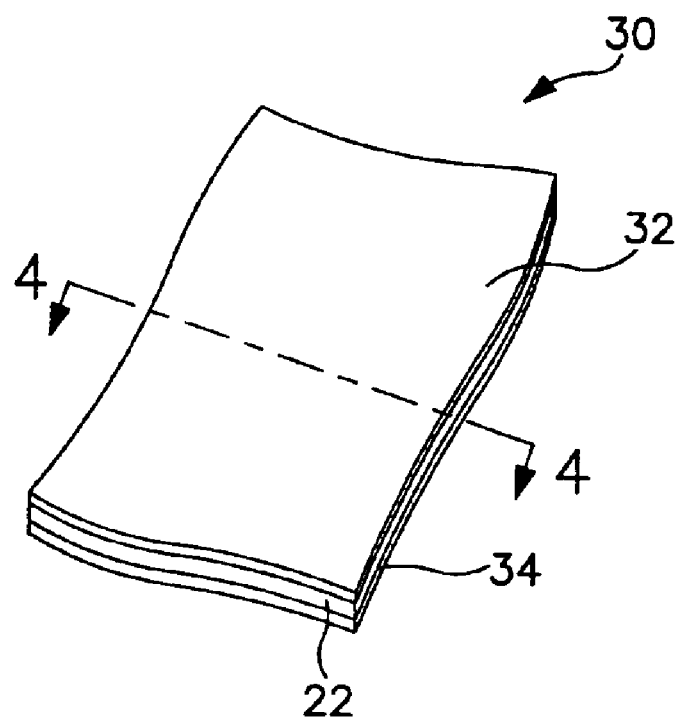
FIG. 3 is a plan view of an elastomeric adhesive laminate of the invention.
Figure 4:
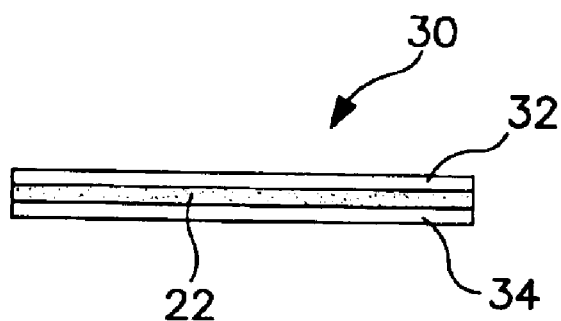
FIG. 4 is a cross-sectional view, taken along line 4—4 of FIG. 3, of another embodiment of an elastomeric adhesive laminate of the invention.

The elastic composite laminates 30 of the invention include the above-described elastomeric adhesive compositions 22 sandwiched between a first facing sheet 32 and a second facing sheet 34, as shown in FIGS. 3 and 4. Facing materials may be nonwoven webs or polymer films formed using conventional processes, including the spunbond and meltblowing processes described in the DEFINITIONS. For example, the facing sheets 32, 34 may each include a spunbonded web having a basis weight of about 0.1–4.0 ounces per square yard (osy), suitably 0.2–2.0 osy, or about 0.4–0.6 osy. The facing sheets 32, 34 may include the same or similar materials or different materials.

If the facing sheets 32, 34 are to be applied to the composition 22 without first being stretched, the facing sheets may or may not be capable of being stretched in at least one direction in order to produce an elasticized area. For example, the facing sheets could be necked, or gathered, in order to allow them to be stretched after application of the elastic composite. Various post treatments, such as treatment with grooved rolls, which alter the mechanical properties of the material, are also suitable for use.

Figure 5:
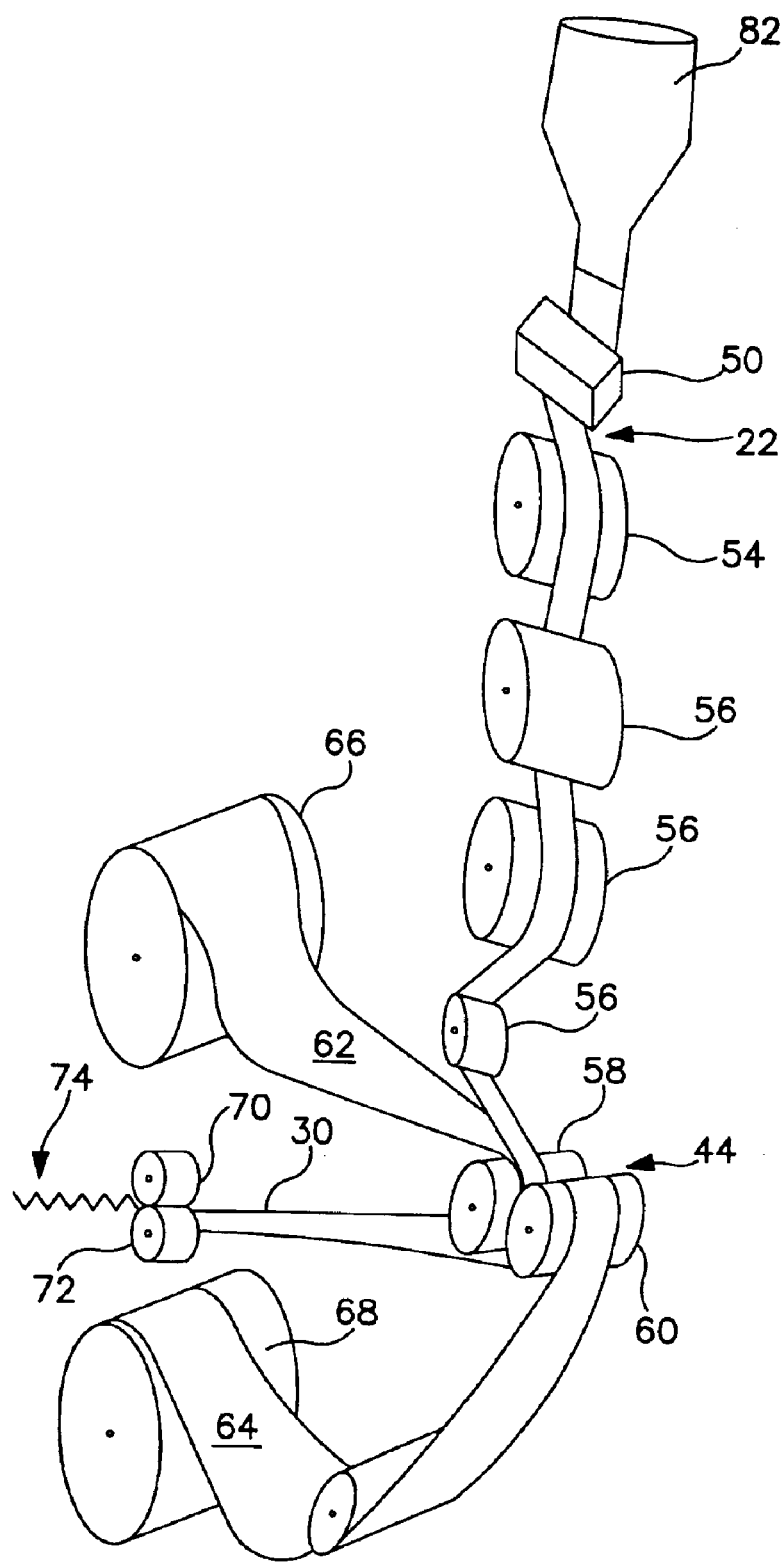
FIG. 5 illustrates a representative process for making the elastomeric compositions and laminates of the invention.

FIG. 5 illustrates a method and apparatus for making an elastomeric adhesive composition and laminate 30 of the invention. While FIG. 5 illustrates a composite VF SBL process it will be appreciated that other processes consistent with the present invention may be used.

The composition is formulated by mixing the base polymer and the tackifier in a Sigma blade batch mixer or by other suitable compounding methods including continuous mixing processes such as twin screw extrusion, resulting in a solid phase composition. Solid blocks of the composition 22 are heated in a melt tank 82 at about 385 degrees Fahrenheit, for example, to form a liquid phase, and then through a slot coat die or an extrusion film die 50 at between about 60 and about 120 grams per square meter (gsm) output before stretching, onto a first chill roll 54 or similar device at between about 10 and about 55 degrees Celsius, for example, in the form of a strand or ribbon. Film output (gsm) denotes grams per square meter as measured by cutting the film with a template and weighing it. The strand or ribbon is then stretched (up to about 1000%) and thinned as the composition 22 is peeled off the first chill roll 54 and passed to one or more first fly rollers 56 towards a nip 44 to form a film. The film 22 may be stretched down to a narrower width and thinned by the first fly rollers 56 during its passage to the nip 44. The nip 44 is formed by opposing first and second nip rollers 58, 60.

The film suitably has a thickness of about 0.001 inch (0.025 mm) to about 0.05 inch (1.27 mm), alternatively of from about 0.001 inch (0.025 mm) to about 0.01 inch (0.25 mm), and a width of from about 0.05 inch (1.27 mm) to about 10 inches (25.4 cm), alternatively of from about 0.5 inch (1.27 cm) to about 5 inches (12.7 cm). The elastomeric, adhesive film 22 may also be capable of imparting barrier properties in an application.

The elastomeric adhesive composition 22 in the form of a film laminate suitably has an elongation of at least 50 percent, alternatively of at least 150 percent, alternatively of from about 50 percent to about 500 percent, and a tension force of less than about 400 grams force per inch (2.54 cm) width, alternatively of less than about 275 grams force per inch (2.54 cm) width, alternatively of from about 100 grams force per inch (2.54 cm) width to about 250 grams force per inch (2.54 cm) width. Tension force, as used herein, is determined one minute after stretching the film laminate to 100% elongation.

In order to form the elastic composite laminate 30, first and second rolls 66 and 68, respectively, of spunbond facing material 62, 64 or other nonwoven or film are fed into the nip 44 on either side of the elastic composition 22 and are bonded by the adhesive present in the elastic composition 22. The facing material 62, 64 might also be made in situ rather than unrolled from previously-made rolls of material. While illustrated as having two lightweight gatherable spunbond facings 62, 64, it will be appreciated that only one facing material, or various types of facing materials, may be used. The elastic composite laminate 30 can be maintained in a stretched condition by a pair of tensioning rollers 70, 72 downstream of the nip 44 and then relaxed as at Ref. No. 74 (FIG. 5).

Figure 6:
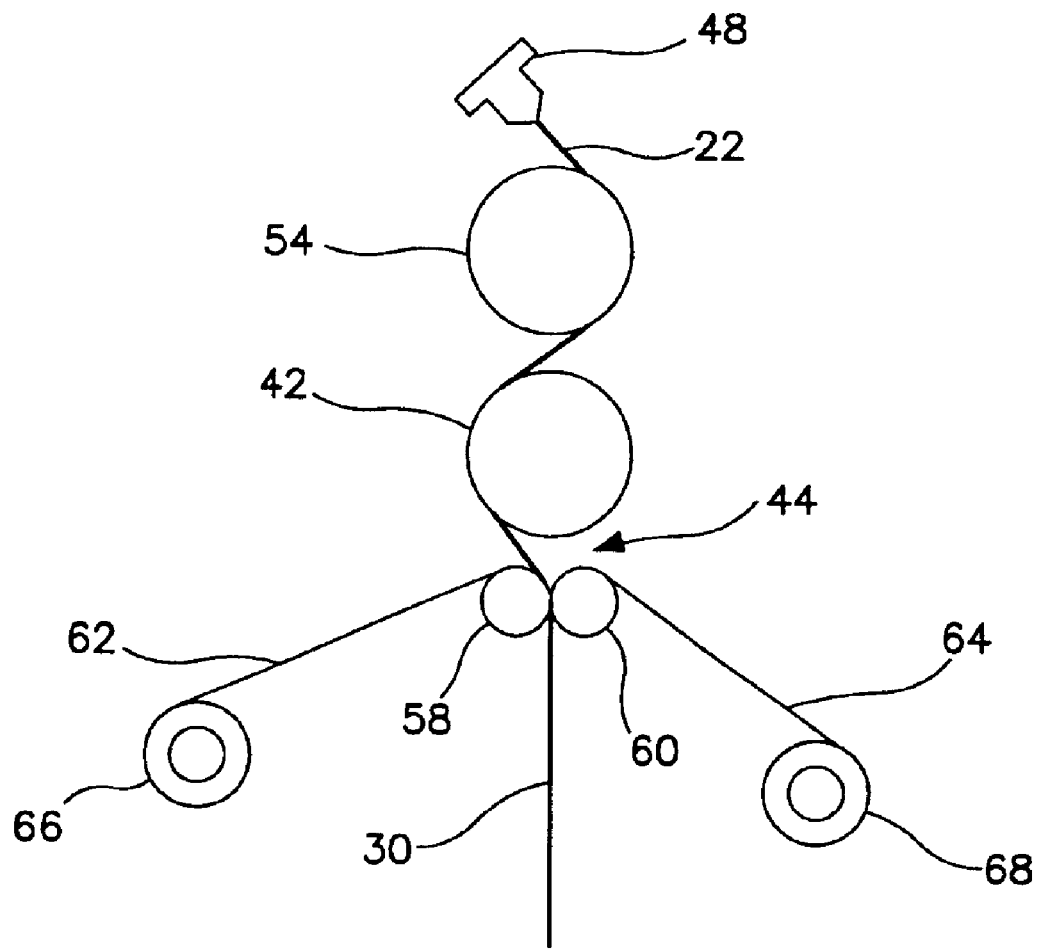
FIG. 6 is a schematic view of another process for making the elastomeric compositions and laminates of the invention.

FIG. 6 illustrates a VF SBL process in which no fly rollers 46, 56 are used. Instead, the elastomeric adhesive composition 22 in the form of a film is extruded onto chill roller 54. The elastomeric adhesive composition 22 is stretched between the chill rollers 42, 54 and the nip 44. Except for the lack of fly rollers, the processes of FIGS. 5 and 6 are similar. In either case, the elastomeric adhesive composition 22 can be laminated between a first facing layer 62 and a second facing layer 64 at the nip 44.

Figure 7:
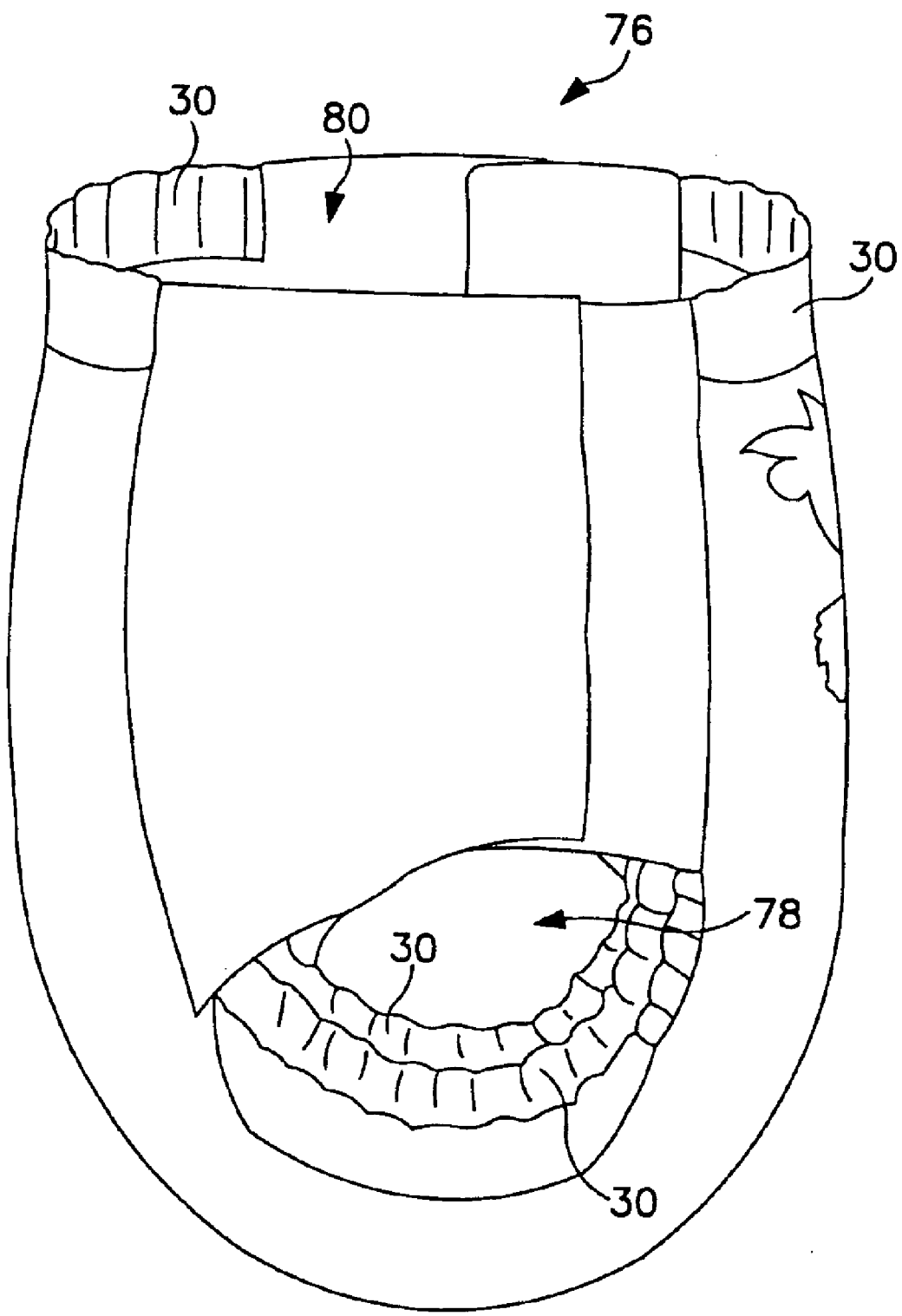
FIG. 7 is a perspective view of a garment having an elastomeric laminate around the leg openings and waist opening.

The resulting elastomeric adhesive compositions and laminates are particularly useful in providing elasticity in personal care absorbent garments 76, as shown in FIG. 7. More specifically, as shown in FIG. 7, the elastomeric adhesive laminates 30 are particularly suitable for use in providing a gasket-like fit around leg openings 78 and waist openings 80. The laminates of this invention are less likely to undergo tension decay or delamination compared to similar laminates incorporating current commercial elastomeric adhesive compositions, as demonstrated in the examples below.

TEST METHODS

Elongation

The elongation of an elastic composite laminate according to the present invention is suitably determined as follows. A 1-inch wide by 4-inch long sample of the laminate is provided. The central 3-inch (7.62 cm) area of the sample is marked. The test sample is then stretched to its maximum length, and the distance between the marks is measured and recorded as the "stretched to stop length." The percent elongation is determined according to the following formula:

{(stretched to stop length (in inches))−3}/3×100

If a 1-inch by 4-inch area is not available, the largest sample possible (but less than 1-inch by 4-inches) is used for testing with the method being adjusted accordingly.

Tension Force

The tension force of an elastic composite laminate according to the present invention is determined on a test sample of the laminate having a width of 1 inch (2.54 cm) and a length of 3 inches (7.62 cm). A test apparatus having a fixed clamp and an adjustable clamp is provided. The adjustable clamp is equipped with a strain gauge commercially available from S. A. Mieier Co. under the trade designation Chatillon DFIS2 digital force gauge. The test apparatus can elongate the test sample to a given length. One longitudinal end of the test sample is clamped in the fixed clamp of the test apparatus with the opposite longitudinal end being clamped in the adjustable clamp fitted with the strain gauge. The test sample is elongated to 100 percent of its elongation (as determined by the test method set forth above). The tension force is read from the digital force gauge after 1 minute. At least three samples of the elasticized area are tested in this manner with the results being averaged and reported as grams force per inch width.

EXAMPLE 1

In this example, several formulations of the elastomeric adhesive composition of the invention were tested for tension decay and/or adhesion.

Composition 1

In this example, the formulated elastomeric adhesive composition of the invention was made up of 55 wt % VECTOR™ 4111 SIS polymer and 45 wt % ESCOREZ™ 5340 tackifier, both available from Exxon-Mobil. ESCOREZ™ 5340 has a softening point of 140 degrees Celsius and viscosity of 5000 cps at 177 degrees Celsius. The composition had an output of 89 gsm before stretching, and was stretched to 600%.

Adhesion of the elastomeric adhesive composition was tested by laminating the composition between two 0.6 osy spunbond facings. A 2-inch wide sample of the laminate, tested at 50% elongation, had a green tension of 136 grams and a permanent set of 12.3%. It was found that no delamination occurred after 2 weeks of aging at 130 degrees Fahrenheit, under a laminate tension of 81.7 grams. After 2 weeks under these conditions, tension loss of the laminate was 40%, and permanent set was 15.7%.

Composition 2

Another elastomeric adhesive composition of the invention was made up of 48 wt % VECTOR™ 4111 SIS polymer, 9 wt % VECTOR™ 4411 SIS polymer, 38 wt % ESCOREZ™ 5340 tackifier, and 5 wt % paraffin wax. This composition had 120 gsm film output before stretching, and was stretched to 800%. The composition was laminated between two 0.6 osy spunbond facings after being extruded through a film die.

An Instron tester, or Sintech tester, or similar instrument, was used to measure tension of a 2-inch sample of the laminate at room temperature. The tension in the laminate during a first cycle was determined to be 167.9 grams (g) at 50% elongation. During retraction of the first cycle, the tension in the laminate was determined to be 68.1 g. The laminate experienced a hysteresis loss of 59.4%. A permanent set for cycle 1 was 18.7%, and a permanent set for cycle 2 was 21%. High permanent set indicates poor elasticity, while low permanent set indicates good elasticity. The laminate experienced no delamination after 2 weeks at 130 degrees Fahrenheit.

Composition 3

This composition had the same formulation as the previous composition, but included ESCOREZ™ 5415 tackifier in place of ESCOREZ™ 5340 tackifier. ESCOREZ™ 5415 has a lower softening point of 118 degrees Fahrenheit, and a lower viscosity of 900 cps at 177 degrees Celsius. Consequently, when tested in the same manner as the previous compositions, namely between two 0.6 osy spunbond facings, this composition was found to have poor adhesion qualities, with the laminate delaminating in 24 hours.

Composition 4

This composition had the same formulation as the two previous compositions, but included ESCOREZ™ 5320 tackifier in place of either ESCOREZ™ 5340 tackifier or ESCOREZ™ 5415 tackifier. ESCOREZ™ 5320 has a relatively low softening point of 122 degrees Celsius, and a relatively low viscosity of 1500 cps at 177 degrees Celsius.

Consequently, when tested in the same manner as the previous compositions, namely between two 0.6 osy spunbond facings, this composition was found to have poor adhesion qualities, with the laminate delaminating in 24 hours.

Composition 5

In this example, the formulated elastomeric adhesive composition of the invention was made up of 65 wt % KRATON® G 2760 SEPS copolymer, available from Kraton Polymers, and 35 wt % PICOLYTE™ S115 tackifier, available from Hercules Inc. The materials were formulated in a Sigma blade batch mixer. The Brookfield viscosity of the formulation was determined to be about 51,000 cps at 380 degrees Fahrenheit. Solid blocks of the adhesive were heated in a melt tank at 385 degrees Fahrenheit and slot coated on a chill roll at 52 degrees Celsius. The process involved peeling off the film from the chill roll while stretching the material up to about 700% at 47 gsm output (before stretching) from the slot coat die. The stretched film was then laminated by nip roll with two nonwoven spunbond webs on each side in a continuous manner.

The laminate appeared to be soft and elastomeric. The green tension value, as measured quickly off-line was in the range of 170–190 grams/inch width. Specifically, 5-inch long specimens were clamped and elongated to 100%. The tension reading was recorded from an electronic gauge one minute after clamping. The tension remaining in the laminate was 100–110 grams/inch width after aging at 130 degrees Fahrenheit for 22 hours. No delamination was observed even after aging at 130 degrees Fahrenheit for an excess of 4 days.

EXAMPLE 2

A series of formulated compositions were produced to compare the effects of low softening point tackifiers versus high softening point tackifiers. A variety of tackifiers having various softening points were used in various combinations, summarized in Table 1. The tackifiers used were:

PICOLYTE™ S25, available from Hercules Inc., having a softening point of 15–25 degrees Celsius, and viscosity of 1,000 cps at 80 degrees Celsius;

PICOLYTE™ S115, available from Hercules Inc., having a softening point of 115 degrees Celsius, and viscosity of 10,000 cps at 150 degrees Celsius; and STAYBELITE™ 5, available from Hercules Inc., having a softening point of 79 degrees Celsius.

These formulated compositions were laminated with 0.6 osy spunbond facings and were then tested for tension decay and delamination. The tension decay was measured by first measuring the "green" tension at 100% elongation of a 2-inch wide, 5-inch long sample. The tension reading was recorded from an electronic gauge one minute after clamping. After aging the samples at 130 degrees Fahrenheit for 1 day, the "aged" tension was then measured in the same manner as the green tension and the resulting aged tension was compared to the green tension to determine whether, or to what extent, tension decay occurred.

It was found that low softening point tackifier alone in the formulation not only caused poor bonding because of low cohesion but also generated low green tension and high tension decay. Results are shown in Table 1.

TABLE 1

Comparison of Tackifiers in Elastic Composite Laminates

| | Tackifier Composition (percentage of total tackifier included in composition) | | | |
| --- | --- | --- | --- | --- |
| Sample | PICOLYTE ™ S25 | PICOLYTE ™ S115 | STAYBELITE ™ 5 | Observations |
| 1 | 100% | — | — | Delaminated in 10 minutes |
| 2 | — | 100% | — | No delamination |
| 3 | 25% | 75% | — | Green tension decreased 20–40%; tension decay was more than 60% after aging at 130° F. for 22 hours; delaminated within 24 hours |
| 4 | 25% | — | 75% | Green tension = 210 g/in width; 100% tension decay after aging at 130° F. for 22 hours; delaminated within 24 hours |

These results confirm that high softening point tackifiers are critical for elastomeric adhesive tension control and adhesion improvement in addition to base polymer choice.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. An elastomeric construction adhesive composition that can be used to create a bonded, elasticized region, comprising:

between about 55% and about 65% by weight base polymer selected from the group consisting of polystyrene-polyethylene-polypropylene-polystyrene (SEPS) block copolymer, styrene-isoprene-styrene (SIS,) styrene-butadiene-styrene (SBS) block copolymer, and combinations thereof, the base polymer having a melt flow rate between about 5 and about 100 grams per minute, a Shore A hardness between about 20 and about 70, and may be stretched up to about 1300%; and a high softening point tackifier resin including at least one type of hydrocarbon selected from a group consisting of petroleum distillates, rosin, rosin esters, polyterpenes derived from wood, polyterpenes derived from synthetic chemicals, and combinations thereof, the tackifier having a softening point of at least 80 degrees Celsius, and a viscosity of at least 1500 cps at 182 degrees Celsius;

wherein the elastomeric adhesive composition has a viscosity of about 5,000 to 80,000 cps at between 177 and 204 degrees Celsius and can be stretched prior to lamination.

2. The composition of claim 1, wherein the base polymer comprises a styrene content of between about 15% and about 45% by weight.

3. The composition of claim 1, wherein the base polymer comprises a styrene content of between about 18% and about 30% by weight.

4. The composition of claim 1, wherein the high softening point tackifier is present in the composition in an amount of at least about 30% by weight.

5. The composition of claim 1, further comprising a low softening point additive having a softening point of less than 80 degrees Celsius and a viscosity of less than 1000 cps at 182 degrees Celsius, present in an amount between about 0% and about 20% by weight.

6. The composition of claim 1, further comprising an antioxidant in an amount between about 0.1% and about 1.0% by weight.

7. The composition of claim 1, wherein the composition can be stretched up to about 1300% prior to lamination.

8. The composition of claim 1, wherein the composition can be stretched up to about 1000% prior to lamination.

9. The composition of claim 1, wherein the composition can be stretched up to about 700% prior to lamination.

10. The composition of claim 1, wherein the composition can be stretched up to about 500% prior to lamination.

11. The composition of claim 1, wherein the composition has a viscosity of about 10,000 to 50,000 cps at between 177 and 196 degrees Celsius.

12. The composition of claim 1, wherein the composition is formed as a plurality of extruded strands.

13. The composition of claim 1, wherein the composition is formed as an extruded film.

14. The composition of claim 1, wherein the composition is formed as a combination of a plurality of extruded strands and an extruded film.

15. The composition of claim 1, wherein the composition can be processed by conventional hot melt equipment.

16. An elastomeric laminate, comprising:
first and second facing sheets; and
an elastomeric adhesive composition between the first and second facing sheets thereby permanently bonding the first and second facing sheets to one another and providing elasticity in the bonded area, the elastomeric adhesive composition including between about 55% and about 65% by weight base polymer selected from the group consisting of polystyrene-polyethylene-polypropylene-polystyrene (SEPS) block copolymer, styrene-isoprene-styrene (SIS), styrene-butadiene-styrene (SBS) block copolymer, and combinations thereof; and a high softening point tackifier resin including at least one type of hydrocarbon selected from a group consisting of petroleum distillates, rosin, rosin esters, polyterpenes deeerived from wood, polyterpenes derived from synthetic chemicals, and combinations thereof, the tackifier having a softening point of at least 80 degrees Celsius and a viscosity of at least 1500 cps at 182 degrees Celsius; wherein the elastomeric adhesive composition has a viscosity of about 5,000 to 80,000 cps at between 177 and 204 degrees Celsius.

17. The elastomeric laminate of claim 16 wherein at least one of the first and second facing sheets comprises a nonwoven web selected from a spunbond web and a meltblown web.

18. The elastomeric laminate of claim 16, wherein at least one of the first and second facing sheets comprises a film.

19. The elastomeric laminate of claim 16, wherein the base polymer comprises a styrene content of between about 15% and about 45% by weight.

20. The elastomeric laminate of claim 16, wherein the base polymer comprises a styrene content of between about 18% and about 30% by weight.

21. The elastomeric laminate of claim 16, wherein the base polymer has a melt flow rate between about 5 and about 100 grams per minute, a Shore A hardness between about 20 and about 70, and may be stretched up to about 1300%.

22. The elastomeric laminate of claim 16, wherein the high softening point tackifier is present in the composition in an amount of at least about 30% by weight.

23. The elastomeric laminate of claim 16, further comprising a low softening point additive having a softening point of less than 80 degrees Celsius and a viscosity of less than 1000 cps at 182 degrees Celsius present in an amount between about 0% and about 20% by weight.

24. The elastomeric laminate of claim 16, further comprising an antioxidant in an amount between about 0.1% and about 1.0% by weight.

25. The elastomeric laminate of claim 16, wherein the composition can be stretched up to about 1200% prior to lamination.

26. The elastomeric laminate of claim 16, wherein the composition can be stretched up to about 1000% prior to lamination.

27. The elastomeric laminate of claim 16, wherein the composition can be stretched up to about 700% prior to lamination.

28. The elastomeric laminate of claim 16, wherein the composition can be stretched up to about 500% prior to lamination.

29. The elastomeric laminate of claim 16, wherein the composition has a viscosity of about 10,000 to 50,000 cps at between 177 and 196 degrees Celsius.

30. The elastomeric laminate of claim 16, wherein the composition is formed as a plurality of extruded strands.

31. The elastomeric laminate of claim 16, wherein the composition is formed as an extruded film.

32. The elastomeric laminate of claim 16, wherein the composition is formed as a combination of a plurality of extruded strands and an extruded film.

33. The elastomeric laminate of claim 16, further comprising:
a garment incorporating the elastomeric laminate into a structure of the garment.

34. The elastomeric laminate of claim 33, wherein the garment is one selected from a group consisting of personal care garments, medical garments, and industrial workwear garments.

35. The elastomeric laminate of claim 34, wherein the garment is one selected from a group consisting of diapers, training pants, swim wear, absorbent underpants, adult incontinence products, feminine hygiene products, protective medical gowns, surgical medical gowns, caps, gloves, drapes, face masks, laboratory coats, and coveralls.

36. A method of making an elastomeric adhesive composition, comprising:

forming a solid phase composition of about 55–65% by weight of a base polymer selected from the group consisting of polystyrene-polyethylene-polypropylene-polystyrene (SEPS) block copolymer, styrene-isoprene-styrene (SIS), styrene-butadiene-styrene (SBS) block copolymer, and combinations thereof, and having a melt flow rate between about 5 and about 100 grams per minute, a Shore A hardness between about 20 and about 70, and stretchable by up to about 1300%; and a high softening point tackifier resin including at least one type of hydrocarbon selected from a group consisting of petroleum distillates, rosin, rosin, esters, polyterpenes derived from wood, polyterpenes derived from synthetic chemicals, and combinations thereof, and having a softening point of at least 80 degrees Celsius and a viscosity of at least 1500 cps at 182 degrees Celsius forming a liquid phase composition by heating the solid phase composition;

forming a film by extruding the liquid phase composition onto a chill roll; and peeling the film off the chill roll while stretching the film;

wherein the elastomeric adhesive composition has a viscosity of about 5,000 to 80,000 cps at between 177 and 204 degrees Celsius, and can be stretched prior to lamination.

37. The method of claim 36, wherein the liquid phase composition is extruded through a slot coat die onto the chill roll.

38. The method of claim 37, comprising stretching the film at an output of between about 50 and about 120 grams per square meter before stretching, from the slot coat die.

39. The method of claim 36, comprising stretching the film up to about 1200%.

40. The method of claim 36, comprising stretching the film up to about 1000%.

41. The method of claim 36, comprising stretching the film up to about 700%.

42. The method of claim 36, comprising stretching the film up to about 500%.

43. The method of claim 36, wherein the liquid phase composition is extruded through an extrusion die onto the chill roll.

44. The method of claim 43, comprising stretching the film at an output of between about 50 and about 120 grams per square meter, before stretching, from the extrusion die.

45. The method of claim 36, further comprising laminating the stretched film between two facing sheets.

46. The method of claim 45, wherein at least one of the facing sheets comprises a non-woven web.

47. The method of claim 45, wherein at least one of the facing sheets comprises a film.

48. The method of claim 36, wherein the liquid phase composition is formed by heating the solid phase composition at between about 177 and about 204 degrees Celsius.

49. The method of claim 36, wherein the chill roll is set at a temperature of between about 10 and about 50 degrees Celsius while the film is being formed.

50. The method of claim 36, wherein the base polymer comprises a styrene content of between about 15% and about 45% by weight.

51. The method of claim 36, wherein the base polymer comprises a styrene content of between about 18% and about 30% by weight.

52. The method of claim 36, wherein the solid phase composition further comprises a low softening paint additive having a softening point of less than 80 degrees Celsius and a viscosity of loss than 1000 cps at 182 degrees Celsius, present in an amount between about 0% and about 20% by weight.

53. The method of claim 36, wherein the solid phase composition further comprises an antioxidant in an amount between about 0.1% and about 1.0% by weight.

54. The method of claim 36, comprising forming the film into a plurality of extruded strands.

55. A garment having an elastomeric adhesive composition therein which is made by a process comprising:

forming a solid phase composition of between about 55% and about 63% by weight base polymer selected from the group consisting of polystyrene-polyethylene-polypropylene-polystyrene (SEPS) block copolymer, styrene-isoprene-styrene (SIS), styrene-butadiene-styrene (SBS) block copolymer, and combinations thereof and a high softening point tackifier resin which includes at least one type of hydrocarbon selected from a group consisting of petroleum distillates, rosin, rosin esters, polyterpenes deeerived from wood, polyterpenes derived from synthetic chemicals, and combinations thereof; having a softening point of at least 80 degrees Celsius and a viscosity of at least 1500 cps at 182 degrees Celsius;

forming a liquid phase composition by heating the solid phase composition, wherein the liquid phase composition has a viscosity of about 5,000 to 80,000 cps at between 177 and 204 degrees Celsius;

forming a film by extruding the liquid phase composition onto a chill roll;

peeling the film off the chill roll while stretching the film; and applying the film between first and second facing sheets, thereby permanently bonding the first and second facing sheets to one another and providing elasticity in the bonded area.

* * * * *